(12) United States Patent
Hiroshige et al.

(10) Patent No.: US 9,999,749 B2
(45) Date of Patent: *Jun. 19, 2018

(54) CATHETER

(71) Applicant: ASAHI INTECC CO., LTD., Nagoya-shi, Aichi (JP)

(72) Inventors: Tadanori Hiroshige, Seto (JP); Makoto Nishigishi, Owariasahi (JP); Kenji Kaneda, Kasugai (JP); Tatsuhiko Kajii, Seto (JP)

(73) Assignee: ASAHI INTECC CO., LTD., Nagoya (JP)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/358,262

(22) Filed: Nov. 22, 2016

(65) Prior Publication Data

US 2017/0072166 A1    Mar. 16, 2017

Related U.S. Application Data

(63) Continuation of application No. 14/100,943, filed on Dec. 9, 2013, now Pat. No. 9,545,496.

(30) Foreign Application Priority Data

Jan. 30, 2013  (JP) ................................ 2013-015013

(51) Int. Cl.
*A61M 25/00*    (2006.01)

(52) U.S. Cl.
CPC ...... *A61M 25/0068* (2013.01); *A61M 25/005* (2013.01); *A61M 25/0012* (2013.01); *A61M 25/0051* (2013.01); *A61M 25/0052* (2013.01); *A61M 25/0053* (2013.01); *A61M 25/0045* (2013.01)

(58) Field of Classification Search
CPC .................... A61M 25/0045; A61M 25/0012
See application file for complete search history.

(56) References Cited

U.S. PATENT DOCUMENTS

| 4,817,613 A | 4/1989 | Jaraczewski et al. |
| 5,667,499 A | 9/1997 | Welch et al. |
| 6,083,257 A | 7/2000 | Taylor et al. |

(Continued)

FOREIGN PATENT DOCUMENTS

| CA | 2660412 A1 | 2/2008 |
| EP | 0732117 A2 | 9/1996 |

(Continued)

OTHER PUBLICATIONS

Jan. 4, 2016 Office Action issued in U.S. Appl. No. 14/100,943.

(Continued)

*Primary Examiner* — Nathan R Price
*Assistant Examiner* — Anh Bui
(74) *Attorney, Agent, or Firm* — Oliff PLC

(57) ABSTRACT

A catheter includes an inner layer, and a braid provided on an outer periphery of the inner layer. The braid includes a first wire and a second wire that are woven together. The catheter further includes a tip provided on a distal end of the inner layer and a distal end of the braid. A residual portion having a sharp shape formed at a distal end of the first wire when the first wire is cut is not left untreated, but is formed into a bulging portion.

12 Claims, 8 Drawing Sheets

(56) References Cited

U.S. PATENT DOCUMENTS

| | | |
|---|---|---|
| 6,562,022 B2 | 5/2003 | Hoste et al. |
| 7,905,877 B1 | 3/2011 | Jimenez et al. |
| 8,366,699 B2 | 2/2013 | Jimenez et al. |
| 8,986,284 B2 * | 3/2015 | Kuwada ............. A61M 25/005 604/524 |
| 9,545,496 B2 * | 1/2017 | Hiroshige ......... A61M 25/0012 |
| 2002/0072729 A1 | 6/2002 | Hoste et al. |
| 2003/0216642 A1 | 11/2003 | Pepin et al. |
| 2005/0010194 A1 | 1/2005 | Zhou |
| 2008/0125752 A1 | 5/2008 | Gunderson et al. |
| 2010/0016837 A1 | 1/2010 | Howat |
| 2013/0018318 A1 | 1/2013 | Ravichandran et al. |
| 2013/0131641 A1 | 5/2013 | Jimenez et al. |
| 2013/0255062 A1 | 10/2013 | Howat |

FOREIGN PATENT DOCUMENTS

| | | |
|---|---|---|
| EP | 0732117 B1 | 8/1999 |
| EP | 0 858 299 B1 | 3/2002 |
| EP | 1 509 273 B1 | 1/2009 |
| EP | 2061541 A1 | 5/2009 |
| JP | 11-514536 | 12/1999 |
| JP | 3057851 | 4/2000 |
| JP | 3184086 B2 | 7/2001 |
| JP | 2002-315834 A | 10/2002 |
| JP | 2005-230318 A | 9/2005 |
| JP | 2005-525883 A | 9/2005 |
| JP | 2006-181258 A | 7/2006 |
| JP | 2012196275 A | 10/2012 |
| JP | 2012249811 A | 12/2012 |
| WO | 00/43061 A1 | 7/2000 |
| WO | 2008/019236 A1 | 2/2008 |
| WO | 2011/008738 A1 | 1/2011 |
| WO | 2012061657 A2 | 5/2012 |

OTHER PUBLICATIONS

Dec. 21, 2015 Office Action issued in Japanese Patent Application No. 2013-015013.
Apr. 7, 2016 Office Action Issued in U.S Appl. No. 14/100,943.
Mar. 3, 2016 Third Party Submission in Japanese Patent Application No. 2013-15013.
Jun. 2, 2016 Office Action Issued in U.S Appl. No. 14/100,943.
Jun. 29, 2016 Office Action issued in Japanese Patent Application No. 2013-015013.
Oct. 10, 2016 Office Action issued in Chinese Patent Application No. 201410010309.9.
May 8, 2014 Search Report issued in European Patent Application No. 14152295.3.
Dec. 20, 2013 Extended Search Report issued in European Patent Application No. 13173132.5-1506.
Nov. 5, 2014 Office Action issued in Japanese Patent Application No. 2012-174528.

* cited by examiner

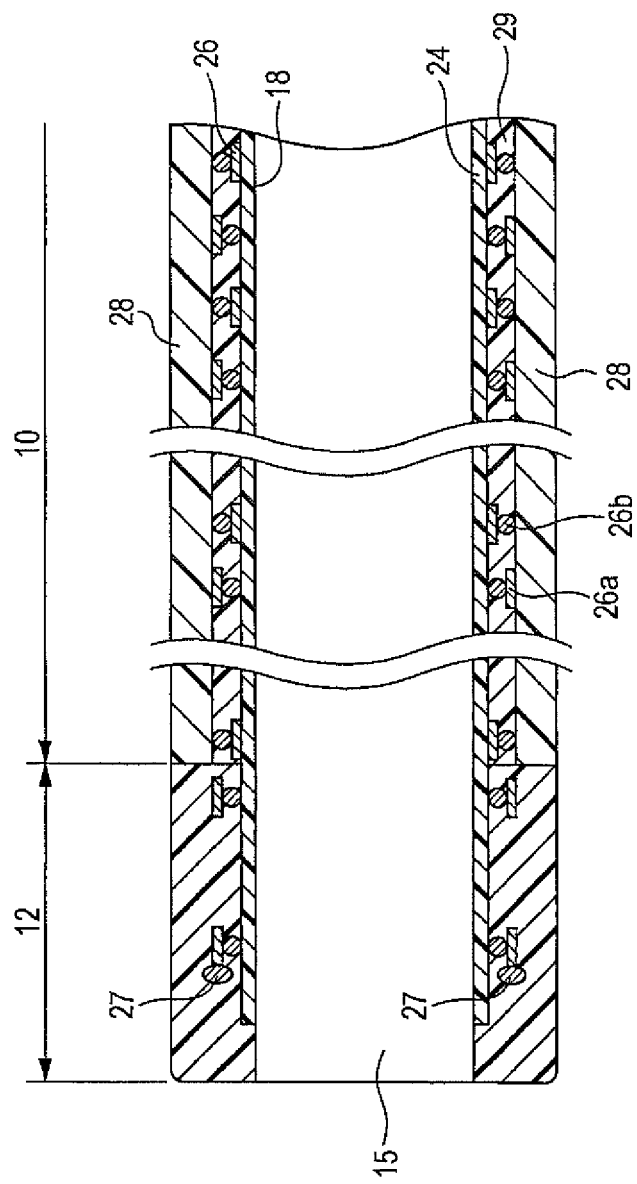

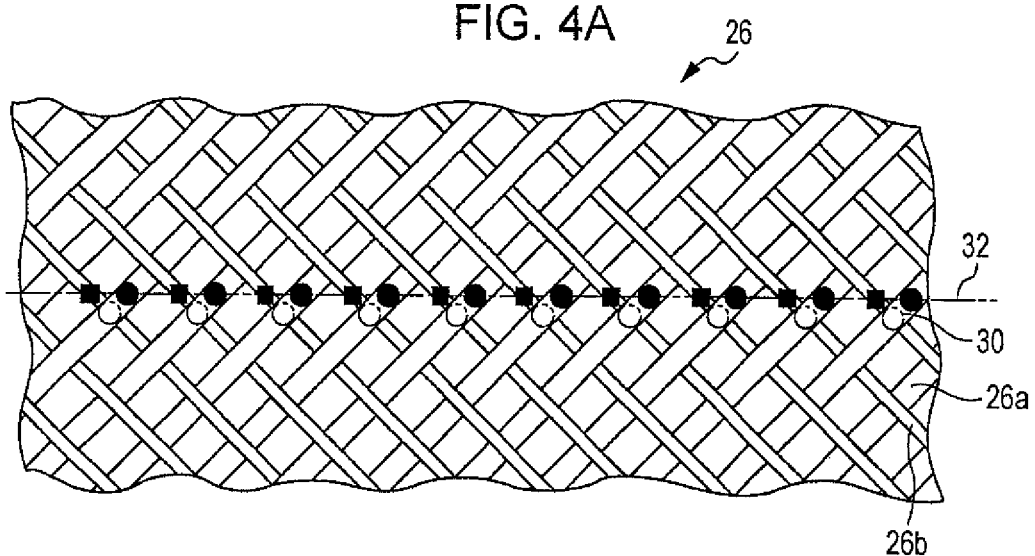
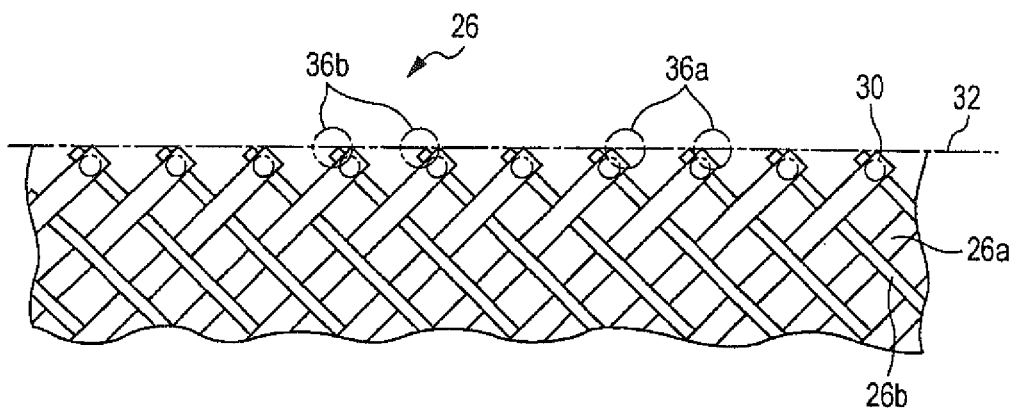
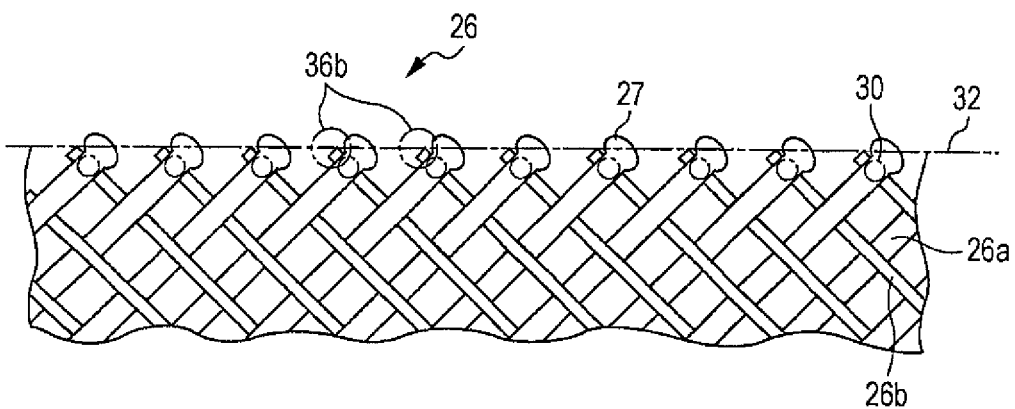

CATHETER

CROSS-REFERENCE TO RELATED APPLICATION

This application is a continuation application of U.S. application Ser. No. 14/100,943, filed Dec. 9, 2013, which claims priority to Japanese Patent Application No. 2013-015013 filed in the Japan Patent Office on Jan. 30, 2013, the entire contents of which are incorporated herein by reference.

BACKGROUND

The disclosed embodiments relate to a medical device. Specifically, the disclosed embodiments relate to catheters to be inserted into a blood vessel, an alimentary canal, a ureter, etc., and more particularly, to a tip of a braid that serves as a reinforcing member of the catheter.

Catheters to be inserted into a blood vessel, an alimentary canal, a ureter, etc., include an inner layer made of a resin, an outer layer that covers the outer periphery of the inner layer and that is made of a resin, and a braid interposed between the inner layer and the outer layer and serves as a reinforcing member. To achieve the performances (pushing performance, torque transmission performance, pressure resistance, etc.) required of the catheters, the braid is generally formed by weaving wires made of a metal, such as tungsten or stainless steel.

The wires included in the braid tend to spread apart at the distal end of the braid owing to the tension of the wires. To prevent this, a braid including a weld portion that extends in the circumferential direction and in which the wires are welded together at the distal end of the braid has been proposed (see, for example, International Publication No. 2008/019236). According to this publication, the weld portion is formed in a region where the wires cross each other, and then excess portions of the wires in a region on the distal side of the weld portion are removed. Thus, the braid including the weld portion that extends in the circumferential direction at the distal end thereof is formed.

SUMMARY

However, according to the above-described method, since the excess portions of the wires are cut off in the weld portion, the area in which the wires are welded together is reduced to half the initial area. Therefore, there is a limit to the welding strength. In particular, with the reduction in size of the catheters, the thickness of the braid tends to be reduced, and reduction in the thickness of the wires leads to a reduction in the welding strength. As a result, there is a risk that the wires included in the braid will spread apart.

In the above-described method, if the wires are cut precisely along the center of the weld portion that extends in the circumferential direction, the wires can be cut without leaving sharp portions at the distal end of the braid. However, in practice, intervals between the wires in the woven state (in other words, intervals between the adjacent wires) are often not uniform owing to variation in the wire pitch that occurs in the weaving process, and it is difficult to cut the wires precisely along the center of the weld portion. When the excess portions of the wires are cut at a position shifted from the center of the weld portion, the wires include sharp portions at the distal end of the braid. Therefore, when a doctor strongly pushes the catheter that has been inserted into a blood vessel, an alimentary canal, a ureter, etc., there is a risk that the distal end of the braid will penetrate the tip. This problem becomes more serious when the catheter is required to be small to reduce the patient's pain and the thickness and length of the tip are reduced accordingly.

The disclosed embodiments have been made in light of the above-described circumstances, and an object of the disclosed embodiments is to provide a catheter in which a sufficient welding strength is ensured between wires of a braid even when the thickness of the wires and the thickness of a tip are reduced, and with which the occurrence of penetration of the braid through the tip can be reduced.

The above-described object can be achieved by the following means.

According to some aspects of the invention, a catheter includes an inner layer; a braid provided on an outer periphery of the inner layer and including a first wire and a second wire, which are woven together, and a bulging portion provided on at least one of a distal end of the first wire and a distal end of the second wire; and a tip provided on a distal end of the inner layer and a distal end of the braid, the tip covering the bulging portion.

In catheters according to the above aspects, at least one of the first wire and the second wire has the bulging portion at the distal end thereof. Thus, the at least one of the first wire and the second wire that has been cut such that a sharp portion is formed is not left untreated, and the risk that the braid will penetrate the tip can be reduced. In addition, since the bulging portion provided at the distal end of the braid functions as an anchor on the tip, the risk that the tip will be pulled off from the catheter shaft can also be reduced.

BRIEF DESCRIPTION OF THE DRAWINGS

FIG. 3 is a sectional view of a distal portion of a catheter shaft and the tip.

FIG. 4A is a plan view of a braid in a state before a cutting process.

FIG. 4B is a plan view of the braid in a state after the cutting process.

FIG. 4C is a plan view of the braid having bulging portions formed at the distal end thereof.

DETAILED DESCRIPTION OF EMBODIMENTS

Figure 1:
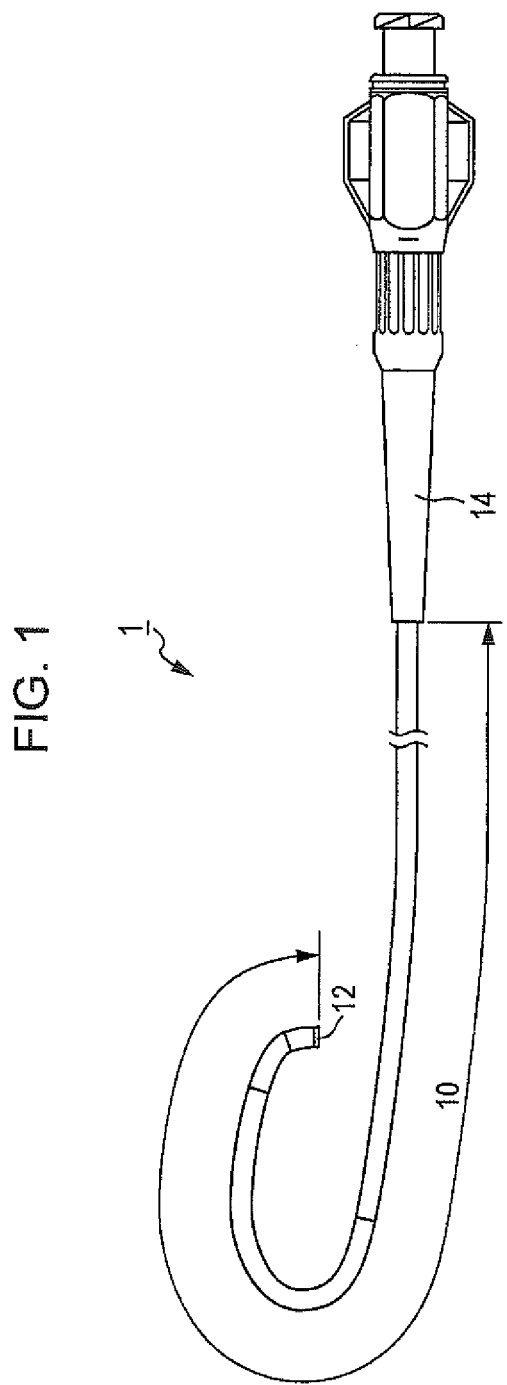
FIG. 1 illustrates the entire body of a catheter according to an embodiment.

A catheter 1 according to an embodiment will be described with reference to FIGS. 1 to 8C. In FIGS. 1 to 3 and 7, a distal end of the catheter 1 that is inserted into a body is shown at the left side, and a proximal end of the catheter 1 that is manipulated by an operator, such as a doctor, is shown at the right side. In each figure, the sizes of components smaller than other components, such as first wires 26a, second wires 26b, bulging portions 27, 37, 47, and 57, etc., of a braid 26, which will be described below, are exaggerated to facilitate understanding.

The catheter 1 illustrated in FIG. 1 is a tubular medical device having an overall length of about 1200 mm. The catheter 1 mainly includes a flexible catheter shaft 10, a tip 12 bonded to the distal end of the catheter shaft 10, and a connector 14 bonded to the proximal end of the catheter shaft 10.

Figure 2:
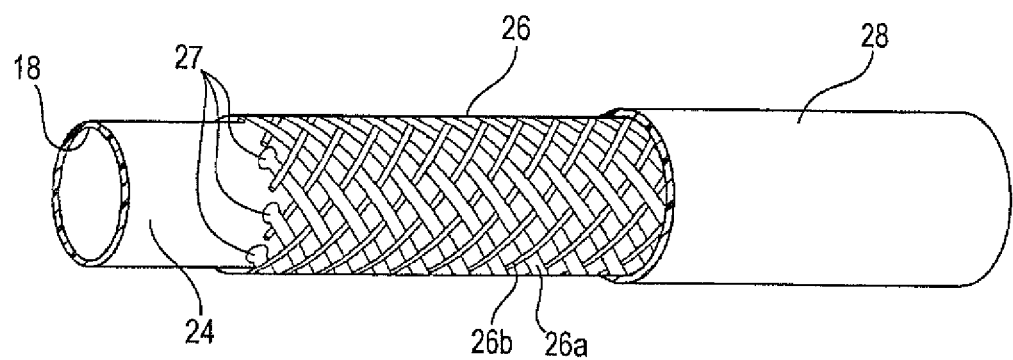
FIG. 2 illustrates a distal portion of the catheter from which a tip and a part of an outer layer are removed for the purpose of explanation.

As illustrated in FIGS. 2 and 3, the catheter shaft 10 includes an inner layer 24, a braid 26 that serves as a reinforcing member, and an outer layer 28 in that order in the radial direction.

The inner layer 24 is made of a resin, and defines a lumen 18 which allows a guidewire or another catheter to be inserted therethrough. The resin material of the inner layer 24 is not particularly limited. In the present embodiment, polytetrafluoroethylene (PTFE) is used.

The braid 26, which serves as a reinforcing member, is formed on the outer periphery of the inner layer 24. As illustrated in FIGS. 2 and 4A to 4C, the braid 26 includes first wires 26a and second wires 26b that are woven in a mesh pattern. In the present embodiment, eight first wires 26a and eight second wires 26b, which are sixteen wires in total (8×8), are woven together. More specifically, the first wires 26a are wound in one direction, and the second wires 26b are wound in another direction.

The combination of the numbers of the first and second wires 26a and 26b of the braid 26 is not limited to 8×8, and may instead be, for example, 4×4 or 2×2 when the numbers are equal to each other, or 4×8 or 2×4 when the numbers are not equal to each other. The first and second wires 26a and 26b may have the same wire width. Alternatively, the wire width of the first wires 26a may be greater than that of the second wires 26b. The first and second wires 26a and 26b are woven such that each wire extends over two wires and under two wires alternately. However, the weave structure is not limited to this, and the first and second wires 26a and 26b may instead be woven such that each wire extends over one wire and under one wire alternately.

The first and second wires 26a and 26b may either be made of the same material or different materials. In the present embodiment, the first wires 26a are made of a stainless steel (SUS316) and have a low melting point, and the second wires 26b are made of tungsten and have a high melting point. However, the materials of the first and second wires 26a and 26b are not particularly limited. For example, materials other than metals (for example, reinforced plastics) may be used. In the present embodiment, the first wires 26a have a rectangular cross section and the second wires 26b have a circular cross section. However, the cross sectional shapes of the first and second wires 26a and 26b are not limited to this. The first and second wires 26a and 26b may both have a rectangular or circular cross section.

As illustrated in FIGS. 2 and 3, bulging portions 27 are provided at the distal ends of the first wires 26a included in the braid 26. The shape of the bulging portions 27 is not particularly limited as long as the bulging portions 27 are not sharp (in other words, as long as the bulging portions 27 have a rounded shape, such as a spherical or elliptical shape).

The outer layer 28, which is made of a resin, is formed on the outer periphery of the braid 26 so as to cover the inner layer 24 and the braid 26. The resin material of the outer layer 28 is not particularly limited, and polyamide, polyamide elastomer, polyester, polyurethane, etc., may be used.

As illustrated in the sectional view of FIG. 3, the entirety of the catheter shaft 10 excluding the tip 12 is covered by the outer layer 28. The outer layer 28 is made of resin materials having different hardnesses so that the flexibility of the outer layer 28 increases toward the distal end from the proximal end of the catheter shaft 10. In FIG. 3, the braid 26 is covered with an intermediate layer 29 made of a resin and the outer layer 28 made of a resin. However, the structure of the braid 26 is not limited to this. The outer diameter of the catheter shaft 10 may be reduced by fanning the catheter shaft 10 without using the intermediate layer 29. The intermediate layer 29 may be made of a resin material that is either the same as or different from the material of the inner layer 24 or the outer layer 28.

In the sectional view of FIG. 3, the catheter shaft 10 is shaped so as to have a constant inner diameter in the axial direction. However, the shape of the catheter shaft 10 is not limited to this. The catheter shaft 10 may instead be tapered such that the diameter thereof increases toward the proximal end and is small only at the distal end.

The tip 12 made of a resin is attached to the distal end of the catheter shaft 10. The tip 12 is a cylindrical member having a distal opening 15. The resin material of the tip 12 is not particularly limited, and polyurethane, polyurethane elastomer, etc., may be used. The tip 12 may contain radiopaque powder. When, for example, the tip 12 contains radiopaque powder (for example, tungsten powder) in the range of about 65 w % to about 90 w %, a doctor, for example, can recognize the accurate position of the catheter 1 during coronary angiography.

The bulging portions 27 provided at the distal end of the braid 26 will now be described.

Referring to FIG. 4A, excess portions of the first and second wires 26a and 26b of the braid 26, in which the first and second wires 26a and 26b are woven together, are cut off by applying a laser beam to a cutting section 32 (in other words, to the first wires 26a at the positions shown by the black circles and to the second wires 26b at the position shown by black rectangles). To prevent the first and second wires 26a and 26b from spreading apart, the first and second wires 26a and 26b are welded together at intersections 30 thereof before the excess portions of the first and second wires 26a and 26b are cut. In FIG. 4A, the first and second wires 26a and 26b are welded together at all of the intersections 30 at the distal end of the braid 26. However, the locations at which the first and second wires 26a and 26b are welded together are not limited to this. When the welding strength between the first and second wires 26a and 26b is sufficient, the first and second wires 26a and 26b may be left unwelded at some of the intersections 30 located at the distal end of the braid 26.

Although the cutting section 32 is shifted from the intersections 30 in FIG. 4A, the position of the cutting section 32 is not limited to this. In the case where the intervals between the wires in the woven state (in other words, intervals between the adjacent wires) are not uniform owing to variation in the wire pitch, the cutting section 32 may extend through some of the intersections 30 instead of extending only through positions shifted from the intersections 30. However, to ensure sufficient welding strength between the first and second wires 26a and 26b, the cutting section 32 is preferably shifted from the intersections 30, as illustrated in FIG. 4A.

Figure 5A:
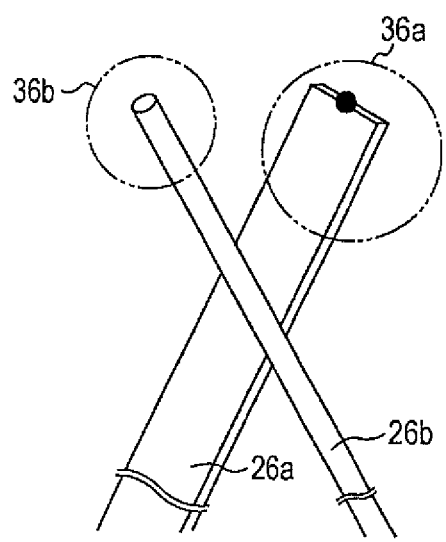
FIG. 5A is a schematic diagram illustrating the distal ends of a first wire and a second wire after the cutting process.

When the excess portions of the first and second wires 26a and 26b are cut off, the first and second wires 26a and 26b have sharp shapes at the cutting section 32, as illustrated in FIGS. 4B and 5A. In the present embodiment, each first wire 26a has a residual portion 36a having a sharp shape at the distal end thereof, and each second wire 26b has a residual portion 36b having a sharp shape at the distal end thereof.

Figure 5B:
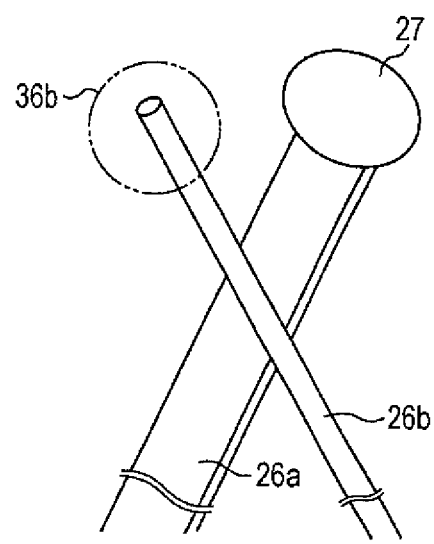
FIG. 5B is a schematic diagram illustrating the state in which a bulging portion is formed at the distal end of the first wire.

Subsequently, the laser beam is applied to the residual portion 36a having a sharp shape (at the position shown by the black circle in FIG. 5A). As a result, as illustrated in FIGS. 4C and 5B, bulging portions 27 are formed which have a rounded shape and which are thicker than the first wires 26a. The bulging portions 27 may be made of a material that is either the same as or different from the material of the first wires 26a. In the case where the bulging portions 27 are made of the same material as that of the first wires 26a, the risk that the bulging portions 27 will be separated from the distal ends of the first wires 26a can be reduced.

The laser beam used to cut the first and second wires 26a and 26b along the cutting section 32 and form the bulging portions 27 is not particularly limited. In the present embodiment, a YAG pulse laser beam is used.

As described above, the residual portions 36a having a sharp shape that are formed at the distal ends of the first wires 26a when the first wires 26a are cut are not left untreated, but are formed into the bulging portions 27 having a rounded shape. Thus, the number of sharp portions of the wires at the distal end of the braid 26 can be reduced. As a result, even when a doctor strongly pushes the catheter I that has been inserted into a blood vessel, the risk that the braid 26 will penetrate the tip 12 can be reduced. In addition, since the bulging portions 27 formed at the distal ends of the first wires 26a are thicker than the first wires 26a, the bulging portions 27 function as anchors on the tip 12. Therefore, the risk that the tip 12 will be pulled off from the catheter shaft 10 can also be reduced. Since the position at which the excess portions of the first wires 26a are cut (in other words, the position of the cutting section 32) is not particularly limited, the above-described structure is useful also when the intervals between the first wires 26a in a woven state are not uniform owing to variation in the wire pitch.

Figure 6A:
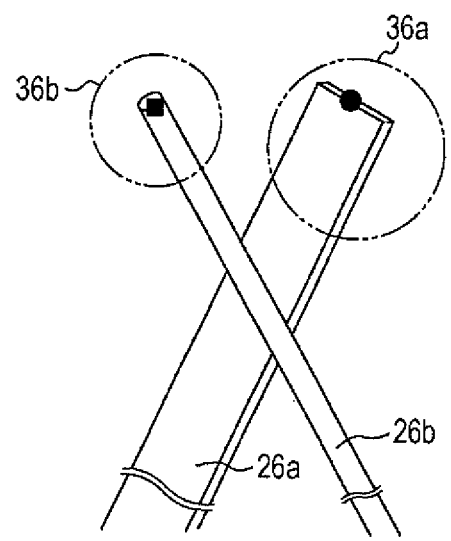
FIG. 6A is a schematic diagram illustrating the distal ends of the first wire and the second wire after the cutting process.
Figure 6B:
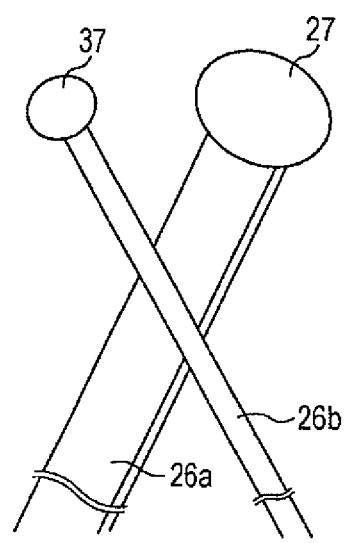
FIG. 6B is a schematic diagram illustrating the state in which a first bulging portion is formed at the distal end of the first wire and a second bulging portion is formed at the distal end of the second wire.

According to the above description, the bulging portions 27 are formed only at the distal ends of the first wires 26a. However, bulging portions are not limited to this. As illustrated in FIGS. 6A and 6B, the laser beam may be applied not only to the residual portion 36a having a sharp shape at the distal end of each first wire 26a (at the position shown by the black circle in FIG. 6A) but also to the residual portion 36b having a sharp shape at the distal end of each second wire 26b (at the position shown by the black rectangle in FIG. 6A), so that the bulging portion 27 is formed at the distal end of each first wire 26a and a bulging portion 37 is formed at the distal end of each second wire 26b.

When the bulging portions 27 made of the same material as the material of the first wires 26a are formed at the distal ends of the first wires 26a and the bulging portions 37 made of the same material as the material of the second wires 26b are formed at the distal ends of the second wires 26b, the risk that the braid 26 will penetrate the tip 12 can be further reduced. In addition, since the bulging portions 27 and 37 are made of the same materials as the materials of the first and second wires 26a and 26b, respectively, the risk that the bulging portions 27 and 37 will be separated from the distal ends of the first and second wires 26a and 26b can be reduced. In addition, since the anchoring effect can be provided by the bulging portions 27 and 37, the risk that the tip 12 will be pulled off from the catheter shaft 10 can be reduced.

Figure 7:
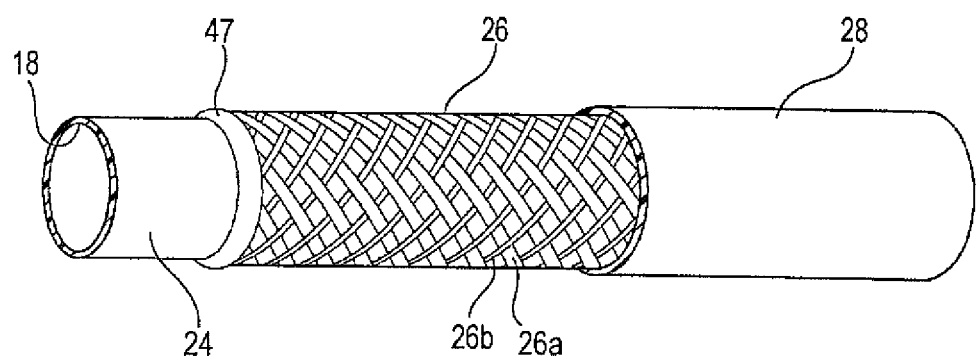
FIG. 7 illustrates an embodiment other than the embodiment illustrated in FIG. 2.

An embodiment other than the embodiment illustrated in FIG. 2 will now be described. Instead of forming the bulging portions 27 and 37 at the distal ends of the first and second wires 26a and 26b, respectively, an annular bulging portion 47 may be formed so as to extend through the distal ends of the first and second wires 26a and 26b, as illustrated in FIG. 7. Since the bulging portion 47 is formed in an annular shape, the first and second wires 26a and 26b may be welded together in a region other than the intersections 30. Therefore, the welding strength between the first and second wires 26a and 26b can be further increased and the thickness of the braid 26 can be reduced.

Although the annular bulging portion 47 is formed so as to extend through the distal ends of both the first wires 26a and the second wires 26b in FIG. 7, the bulging portion 47 is not limited to this. For example, after the excess portions of the first wires 26a are cut off, the bulging portion 47 may be formed so as to extend through the distal ends of the first wires 26a by connecting the residual portions 36a having a sharp shape at the distal ends of the first wires 26a with the same material as the material of the first wires 26a. In addition, the bulging portions 37 may be formed at the distal ends of the second wires 26b, as illustrated in FIG. 6B. Thus, the annular bulging portion 47 may be formed so as to extend through the distal ends of either or both of the first and second wires 26a and 26b, thereby welding either or both of the first and second wires 26a and 26b together. As a result, the first and second wires 26a and 26b of the braid 26 can be prevented from spreading apart.

The material of the bulging portion 47 may be the same as the material of the first wires 26a or the material of the second wires 26b. Alternatively, the material of the bulging portion 47 may be different from the materials of the first and second wires 26a and 26b. For example, when a radiopaque material (for example, gold, platinum, tungsten, or an alloy thereof) is used, the bulging portion 47 functions also as a marker.

Figure 8A:
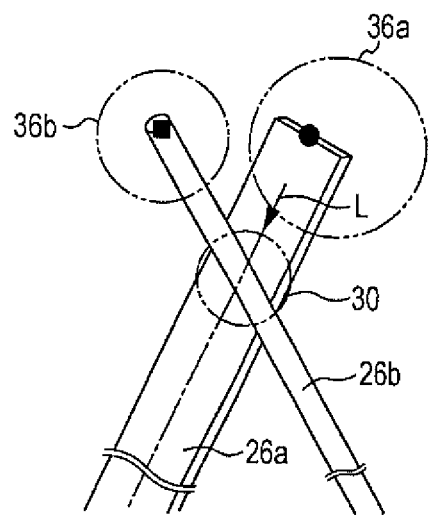
FIGS. 8A to 8C illustrate an embodiment other than the embodiment illustrated in FIGS. 6A and 6B.
Figure 8B:
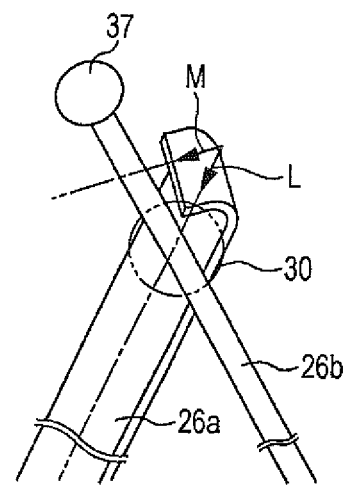
Figure 8C:
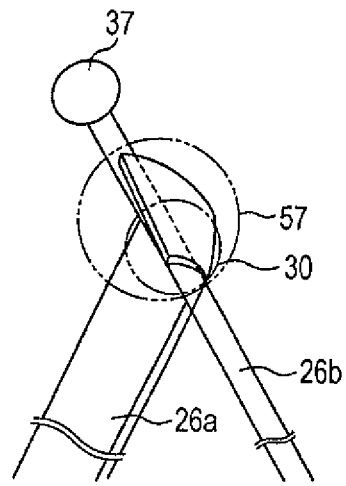

According to the above description, the bulging portions 27, 37, and 47 are provided on the distal ends of either or both of the first and second wires 26a and 26b. However, the bulging portions are not limited to this. As illustrated in FIGS. 8A to 8C, a bulging portion 57 may be formed at the intersection 30 of the first and second wires 26a and 26b. In this example, a laser beam is applied to the residual portion 36a having a sharp shape at the distal end of the first wire 26a (at the position shown by the black circle in FIG. 8A) and the residual portion 36b having a sharp shape at the distal end of the second wire 26b (at the position shown by the black rectangle in FIG. 8A). The conditions, such as the intensity and the position, of the laser beam are adjusted so that the bulging portion 37 is formed at the distal end of the second wire 26b and the bulging portion 57 is formed at the intersection 30. The bulging portion 57 is formed by melting the residual portion 36a having a sharp shape with the energy of the laser beam, causing the residual portion 36a to solidify while moving in an axial direction L of the first wire 26a and a direction M that crosses the axial direction L (see FIG. 8B), and causing the distal end of the first wire 26a to wrap around the side surface of the second wire 26b at the intersection 30 (see FIG. 8C).

As illustrated in FIGS. 8A to 8C, the first wire 26a can be welded to the second wire 26b at the intersection 30 while forming the bulging portion 57 at the distal end of the first wire 26a. Therefore, the step of welding the first and second wires 26a and 26b together at the intersection 30 before cutting off the excess portions of the first and second wires. 26a and 26b can be omitted. As a result, the manufacturing cost of the catheter 1 can be reduced.

As described above, the bulging portions 27, 37, and 47 are provided at the distal end of the braid 26. Thus, the distal ends of either or both of the first wires 26a and the second wires 26b that have been cut into a sharp shape are not left untreated, and the risk that the braid 26 will penetrate the tip 12 can be reduced. In addition, the bulging portions 27, 37, and 47 provided at the distal end of the braid 26 serve as anchors on the tip 12, so that the risk that the tip 12 will be pulled off from the catheter shaft 10 can also be reduced.

What is claimed is:

1. A catheter comprising:
   a catheter shaft including;
      an inner layer;
      a braid disposed on an outer periphery of the inner layer, the braid including (i) a plurality of first wires and a plurality of second wires that are woven together, and (ii) a plurality of first bulging portions disposed on corresponding distal ends of the plurality of first wires; and
      an outer layer disposed on an outer periphery of the braid; and
   a tip disposed on a distal end of the catheter shaft, the tip covering the plurality of first bulging portions,
   wherein each of the plurality of first bulging portions is disposed at a position distally shifted from an intersection that each of the plurality of first wires and each of the plurality of second wire are intersected.

2. The catheter according to claim 1, further comprising:
   a plurality of second bulging portions disposed on corresponding distal ends of the plurality of second wires,
   wherein each of the plurality of second bulging portions is larger than each of the plurality of first bulging portions.

3. The catheter according to claim 2, wherein each of the plurality of second bulging portions is disposed at the intersection.

4. The catheter according to claim 2, wherein each of the plurality of second bulging portions is disposed at a position proximally shifted from each of the plurality of first bulging portions.

5. The catheter according to claim 1, wherein a radial thickness of each of the plurality of first bulging portions is larger than a radial thickness of each of the plurality of first wires.

6. The catheter according to claim 2, wherein a radial thickness of each of the plurality of second bulging portions is larger than a radial thickness of each of the plurality of second wires.

7. A catheter comprising:
   a catheter shaft including;
      an inner layer;
      a braid disposed on an outer periphery of the inner layer, the braid including (i) a first wire and a second wire that are woven together, and (ii) a first bulging portion disposed on a distal end of the first wire; and
      an outer layer disposed on an outer periphery of the braid; and
   a tip disposed on a distal end of the catheter shaft, the tip covering the first bulging portion,
   wherein the first bulging portion is disposed at a position distally shifted from an intersection that the first wire and the second wire are intersected.

8. The catheter according to claim 7, further comprising:
   a second bulging portion disposed on a distal end of second wire,
   wherein the second bulging portion is larger than the first bulging portion.

9. The catheter according to claim 8, wherein the second bulging portion is disposed at the intersection.

10. The catheter according to claim 8, wherein the second bulging portion is disposed at a position proximally shifted from the first bulging portion.

11. The catheter according to claim 7, wherein a radial thickness of the first bulging portion is larger than a radial thickness of the first wire.

12. The catheter according to claim 8, wherein a radial thickness of the second bulging portion is larger than a radial thickness of the second wire.

* * * * *